United States Patent [19]
Lynn

[11] Patent Number: 5,891,023
[45] Date of Patent: Apr. 6, 1999

[54] APPARATUS FOR THE DIAGNOSIS OF SLEEP APNEA

[76] Inventor: Lawrence A. Lynn, 1275 Olentangy River Rd., #223, Columbus, Ohio 43212

[21] Appl. No.: 789,460

[22] Filed: Jan. 27, 1997

Related U.S. Application Data

[63] Continuation of Ser. No. 391,811, Feb. 21, 1995, Pat. No. 5,605,151, which is a continuation of Ser. No. 151,901, Nov. 15, 1993, Pat. No. 5,398,682, which is a continuation-in-part of Ser. No. 931,976, Aug. 19, 1992, abandoned.

[51] Int. Cl.⁶ .................................................. A61B 5/0205
[52] U.S. Cl. .......................... 600/323; 600/484; 600/529
[58] Field of Search .................................... 128/633, 670, 128/671, 716, 719, 721; 600/323, 324, 333, 483, 484, 529, 534, 537, 538, 595

[56] References Cited

U.S. PATENT DOCUMENTS

| | | | |
|---|---|---|---|
| 4,365,636 | 12/1982 | Baker | 128/716 |
| 4,630,614 | 12/1986 | Atlas | 128/721 |
| 5,275,159 | 1/1994 | Griebel | 128/716 |
| 5,385,144 | 1/1995 | Yamanishi et al. | 128/716 |
| 5,398,682 | 3/1995 | Lynn | 128/633 |

OTHER PUBLICATIONS

Longobardo et al., Sleep Apnea Considered As A Control System Instability, Respiratory Physiology Sep. 1982.

Strohl et al. Oxygen Saturation During Breath Holding and During Apneas In Sleep, Chest. Feb. 1984; 85, No. 1; 181–186.

George et al. Identification and Qualification of Apneas by Computer-based Analysis of Oxygen Saturation American Review of Respiratory Disease, 1988; 137: 1238–1240.

Slutsky et al. Quantification of Oxygen Saturation During Episodic Hypoxemia. American Review of Respiratory Disease, 1980; 121:893–895.

Gyulay et al. A Comparison of Clinical Assessment and Home Oximetry in the Diagnosis of Obstructive Sleep Apena. American Review of Respiratory Disease, 1993; 147: 50–53.

Pépin et al. Does Oximetry Contribute to the Detection of Apneic Events? Mathematical Proceeding of the $SaO_2$ Signal. Chest, May 1991; 1151–1157.

Timms et al. Oxygen Saturation by Oximetry: Analysis By Microcomputer, Journal of Polysomnorgraphic Technology, Spring 1988: 13–21.

Rauscher et al. Computerized Detection of Respirtory Events During Sleep from Rapid Increases in Oxyhemoglobin Saturation. Lung, 1991; 169: 355–42.

Rauscher et al. Quantification of sleep–disordered breathing by computerized analysis of oximetry, heart rate, and snoring. Eur Respir J, Jun. 1991; 4: 655–659.

Hoffarth et al. "Beurteilung Pulsoximetrisch erfasster zyklisheer . . . " and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229–232).

Aubry et al. A microcomputer system for monitoring and analyzing oxyhemoglobin saturation during sleep. Computer Programs in Biomedicine. 1984; 18: 227–234.

Fletcher, et al. The Rate of Fall of Arterial Oxyhemoglobin Saturation in Obstructive Sleep Apnea. Chest, 1989; 96: 717–722.

Griffiths, et al. A video system for investigating breathing disorders during sleep. Thorad, 1991; 46: 136–140.

(List continued on next page.)

Primary Examiner—Jennifer Bahr
Assistant Examiner—Eric F. Winakur
Attorney, Agent, or Firm—Fish & Richardson P.C.

[57] ABSTRACT

A device for diagnosing sleep apnea by identifying desaturation and resaturation events in oxygen saturation of a patient's blood. The slope of the events is determined and compared against various information to determine sleep apnea.

51 Claims, 5 Drawing Sheets

OTHER PUBLICATIONS

Hoch, et al. Überprüfung der Früherkennungsmethode MESAM und Biox 3700 zur Erfassung schlafbezogener Atmungsregulationsstörungen bei jungen Männern. Pneumologie, 1991; 45: 217–222 and translation.

Salmi, et al. Evaluation of Automatic Analysis of SCSB, Airflow and Oxygen Saturation Signals in Patients with Sleep Related Apneas. Chest, 1989; 96: 255–61.

Sanders, et al. Obstructive Sleep Apnea Treated by Independently Adjusted Inspiratory and Expiratory Positive Airway Pressures via Nasal Mask. Chest, 1990: 98: 317–24.

Sériés, et al. Utility of Nocturnal Home Oximetry for Case Finding in Patients with Suspected Sleep Apnea Hypopnea Syndrome, Annl Int Med, 1993; 119–449–53.

Svanborg, et al. A Limited Diagnostic Investigation for Static Charge Sensitive Bed. Chest, 1990: 98: 1341–45.

Kirby, et al. Computer quantitation of saturation impairment time as an index of oxygenation during sleep Comp Meth, 1992; 107–115.

"Evaluation of Obstructive Sleep Apnoea in Singapore Using Computerised Polygraphic Monitoring" W.C. Tan and T.H.Koh, *Annals Academy of Medicine*, Mar. 1991, vol. 20 No. 2 pp. 196–200.

"Unattended CPAP Titration: Toward a Smart Machine" G. Guilleminault, R. Stopha, L. Milea, J. Catiman, E. Kaitkawski,.

Sériès, et al., Influence of Continuous Positive Airway Pressure on Sleep Apnea–Related Desaturation in Sleep Apnea Patients. Lung, 1992; 170: 281–290.

APPARATUS FOR THE DIAGNOSIS OF SLEEP APNEA

This application is a continuation of U.S. patent application Ser. No. 08/391,811, filed Feb. 21, 1995, now U.S. Pat. No. 5,605,151 which is a continuation of U.S. patent application Ser. No. 08/151,901 filed Nov. 15, 1993, now U.S. Pat. No. 5,398,682 which is a continuation-in-part of application Ser. No. 08/931,976, filed Aug. 19, 1992, abandoned.

BACKGROUND AND SUMMARY OF THE INVENTION

Disorders of breathing during sleep are now known to constitute a major health problem throughout the world. Obstructive sleep apnea is an extremely common disease which manifests itself in variable degrees of severity. The disease develops when muscle tone of the upper airway diminishes during sleep and negative pressures associated with inspiration result in collapse of the upper airway, preventing air movement and resulting in airway obstruction. The sleeping patient inhales more forcibly, thereby, further lowering upper airway pressures and causing further collapse of the upper airway. During this time, substantially no air movement into the chest occurs and the patient becomes progressively more hypoxic and hypercarbic. Both hypoxemia and hypercarbia produce central nervous system stimulation resulting in arousal. Upon arousal, increase in airway muscle tone opens the airway and the patient rapidly inhales and ventilates quickly to correct the abnormal arterial blood gas values. Generally, the arousal is only modest and the patient is not aware of the arousal. Once blood gas parameters have been corrected, the patient begins to sleep more deeply, upper airway tone again diminishes, and the upper airway collapses resulting in sequential and cyclic apneic arousal episodes.

The duration and severity of each apnea is quite variable from patient to patient and with the same patient throughout the night. Indeed, the disease process represents a spectrum of severity from mild snoring, which is associated with incomplete and inconsequential airway obstruction, to severe apneas which can result in fatal hypoxemia.

This disease commonly results in excessive daytime sleepiness and can disrupt cognitive function during the day due to fragmentation of sleep during the night associated with recurrent arousals of which the patient is not aware.

Although this disease commonly affects obese patients, it may occur in patients with any body habitus. Because this disease is so common and because it presents with the subtle and common symptoms of excessive daytime sleepiness, morning headache, and decreasing ability to concentrate during the day, it is critical that an inexpensive technique for accurately diagnosing and treating this disease be developed. Traditionally, this disease has been diagnosed utilizing a complex and expensive multi-channel polysomnogram as the first diagnostic step. This is generally performed in a sleep lab and involves the continuous and simultaneous measurement and recording of an encephalogram, electromyogram, extraoculogram, chest wall plethysmogram, electrocardiogram, measurements of nasal and oral air flow, and pulse oximetry. These, and often other, channels are measured simultaneously throughout the night and these complex recordings are then analyzed to determine the presence or absence of sleep apnea. From the perspective of the primary care physician, the identification of patients with obstructive sleep apnea (OSA) with a primary care practice represents a daunting challenge. This challenge is derived primarily by the fact that OSA represents with extraordinarily common signs and symptoms. These include varying degrees of daytime sleepiness (which may be difficult to distinguish historically from fatigue), inability to concentrate, irritability, headache, and habitual snoring. In addition, the physical findings of OSA are also common and include hypertension, lower extremity swelling, and obesity. Any of these signs may be completely absent and the patient may appear entirely normal to the physician.

There are, therefore, no clear distinguishing historical or physical finds of OSA. In fact, a recent study has shown specificity and sensitivity of clinical evaluation alone to be only 60% and 63%, respectively. The complete lack of sensitivity and specificity of clinical evaluation for the disease is confounded by the fact that it occurs so frequently in specific population groups. In the U.S., OSA is a co-morbin condition in up to 20% of patients with coronary artery disease and 30% of patients with hypertension. The primary care physician, understanding the frequency of this association and the lack of sensitivity of clinical evaluation, is faced with the clear recognition that the majority of patients with OSA within any primary care practice will remain undiagnosed unless a prohibitive number of patients are evaluated by polysomnography.

Since OSA is more common than diabetes and its symptoms are just as subtle, it is critical that all primary care physicians have an inexpensive test which helps assess the pretest probability of the disease. The optimal diagnostic system should easily fall within the budget of the primary care physician for capital expenditures (e.g., $500–$1000) and should be able to be performed within the requirement of complex patient attachments and additional medical technologists, which many primary care physicians would find prohibitive. Indeed, the ideal system would not require complex setup in the home, but rather would require only very simple instructions to the patient. Furthermore, the test should be repeatable, as with a weekend study at no additional cost to the primary care physician, so that multiple consecutive nights could be recorded to assess night-to-night variability in selected patients. In addition, and perhaps most important, patient costs for a diagnostic study should be less than $100 for a single or multiple consecutive night evaluation.

It is also optimal that the home test not be duplicative of conventional polysomnography which, because of its complexity, is best performed in a laboratory setting. On the contrary, the ideal home system would be synergistic with laboratory polysomnography. It is considered advantageous to avoid the use of "mini-polysomnograms" in the home environment. It has been suggested that such conventional multi-channel home systems may actually increase the number of in-lab studies to be performed to "sort out" abnormal home studies (see New Directions for Pulse Oximetry in Sleep Disorders. *Mayo Clinic Proceedings*, Tobert et al. June 1995; 70:591–92). Furthermore, HMOs and insurance carriers often consider the conventional home multi-channel home studies are done first. Furthermore, in actual practice, such home multi-channel studies often must be repeated or require home setup by a trained medical technologist, which greatly increases the expense.

The issue of sensitivity and specificity with respect to an OSA home diagnostic system must be placed in perspective since the disease is relatively unique in that the "state of disease" is not finite. It is important to recognize that, with OSA there is no clear definition of the lowest threshold of severity which constitutes disease. Indeed, in a recent study, 26% of middle-age adult males met the minimum criteria for OSA based on the apnea/hypopnea index alone. Clearly, a gray area exists between normal and milder forms of airway instability and heightened airway resistance which may or may not require therapy. Indeed, home diagnostic systems which positively identify patients with heightened airway resistance or very mild or normal levels of OSA may simply increase cost through the identification of the vast pool of patients for which further diagnostic evaluation and intervention has no clearly definable indication (again, see New Directions for Pulse Oximetry In Sleep Disorders, *Mayo Clinic Proceedings*. Tobert et al. June 1995; 70:591–92). The critical challenge is to identify the vast number of undiagnosed patients having OSA of significant severity such that therapeutic intervention has established efficacy. These are the patients most likely to develop the cardiovascular sequelae of OSA.

Furthermore, the increased risk of automobile accidents is directly correlated with severity of disease. The ideal home diagnostic system should be selectively sensitive for disease of significant severity such that treatment has established efficacy.

The problem with this traditional approach of using the sleep lab as a first test for case-finding is that such complex sleep testing costs between one-thousand to thirty five hundred dollars. The available resources for performing the procedure are relatively scarce. Since the patients often perceive the symptoms (e.g. sleepiness) as non-life threatening, many patients find the cost for the evaluation prohibitive, even if the physicians choose to refer the patient. In addition, primary care physicians managing HMOs with limited equipment budgets will be understandably reluctant to sent patients with subtle symptoms or in high risk groups for such an expensive initial evaluation without first having an inexpensive means to better assess the probability of disease, and thereby better focus these limited resources. For these reasons, the majority of patients with OSA in the U.S. remain undiagnosed. Since sleep apnea is so common, the cost of diagnosing obstructive sleep apnea in every patient having this disease in the United States would exceed Ten Billion Dollars. It is critical that a new, inexpensive technique of accurately diagnosing sleep apnea be developed.

Nocturnal oximetry alone has been used as a screening tool to screen patients with symptoms suggestive of sleep apnea to identify whether or not oxygen desaturations of hemoglobin occur. Microprocessors have been used to summarize nocturnal oximetry recordings and to calculate the percentage of time spent below certain values of oxygen saturation However, oxygen desaturation of hemoglobin can be caused by artifact, hypoventilation, ventilation perfusion mismatching. For these reasons, such desaturations identified on nocturnal oximetry are not specific for sleep apnea and the diagnosis of sleep apnea has generally required expensive formal polysomnography.

The present invention comprises a system and technique for deriving and utilizing the analysis of graphical pulse oximetry-derived waveforms as a function of time to accurately diagnose sleep apnea. This invention is therefore synergistic with conventional sleep lab testing since the convention sleep lab can subsequently be used in a more efficient and focused manner to assure mitigation of arousals and sleep fragmentation by therapy.

It is the purpose of this invention to provide an inexpensive system for the collection and analysis of pulse oximetry values as a function of time during sleep to provide a diagnosis of sleep apnea with a high degree of specificity.

This invention provides a reliable and specific means for the diagnosis of obstructive sleep apnea which can be performed in the patient's home without attendance of technical personnel. It is further the purpose of this invention to provide an inexpensive and accurate means to both screen for and specifically diagnose obstructive sleep apnea by a single overnight recording in the patient's home without the need for multiple connections to different parts of the patient's body. It is further the purpose of this invention to define a technique for diagnosing obstructive sleep apnea utilizing the calculation of the ascending and descending slope ratio of phasic oxygen desaturations measured during sleep.

Specifically, the present invention defines a device for diagnosing sleep apnea, that has the following components. First, a means must determine an oxygen saturation of a patient's blood. This saturation value is coupled to a means for identifying a desaturation event based on the saturation value. The desaturation event is one in which said oxygen saturation falls below a baseline level by a predetermined amount and for a predetermined time. The slope of the event is calculated by means for calculating a slope of said desaturation event representing a rate of change per unit time of fall of oxygen saturation. This slope is used by a means for comparing said calculated slope with a value of slope which is determined in advance to be indicative of sleep apnea, and determination of diagnosis of sleep apnea is made based on said comparing.

The comparing can be done by:
1) comparing with an absolute number which is likely to indicate a sleep apnea, or
2). comparing with other slopes taken at different times.

The identifying means can also identify a resaturation, immediately following said desaturation and coupled with said desaturation, in which the oxygen saturation rises, and wherein the determination can also be based on a slope of said resaturation.

Many other ways of calculating the slope are also disclosed herein.

These and other aspects of the invention will now be described in detail with reference to the accompanying drawings, wherein:

DESCRIPTION OF THE PREFERRED EMBODIMENTS

The inventor of the present invention found, relative to sleep apnea diagnosis, that the waveform pattern of oximetry during a sleep recording can be considered in relation to the physiologic parameters which affect oxygen saturation over time. Specifically, during an apneic period, arterial oxygen saturation initially falls as a function of the oxygen saturation of mixed venous blood and oxygen uptake from residual exchangeable oxygen within the lungs. Subsequently, arterial oxygen saturation falls directly as a function of oxygen consumption and global oxygen stores. These stores of oxygen are very limited. The sources of oxygen available during an apneic period include residual exchangeable oxygen within alveoli and airways, the oxygen bound to hemoglobin, dissolved oxygen within body tissues and oxygen stored as myoglobin. These stores are rapidly depleted during an apneic period as a function of global oxygen consumption. As oxygen stores are depleted, the cellular oxygen levels fall, and mixed venous oxygen saturation progressively diminishes. Since a small amount of exchangeable oxygen supply exists within alveoli and airways, arterial oxygen saturation, as measured by the pulse oximeter is briefly unaffected by the initial fall in body oxygen storage. However, since oxygen stores within the alveoli are extremely limited, arterial oxygen saturation then progressively falls toward that of mixed venous arterial blood saturation since little significant gas exchange occurs as mixed venous blood passes by essentially unventilated alveoli. The partial pressure of oxygen in arterial blood therefore progressively falls toward the mean partial pressure of oxygen in body tissues at the cellular level.

It is possible to measure indirectly the partial pressure of oxygen in arterial blood by measurement of arterial oxygen saturation of hemoglobin utilizing a pulse oximeter 12. If the probe 13 of pulse oximeter is placed on a patient's finger or other body part during a prolonged apneic period, a progressive decrement in arterial saturation will be identified as a function of the fall in arterial oxygen partial pressure. Although the initial decline in arterial oxygen saturation is greatly dependant on mixed venous oxygen saturation, since body oxygen stores during a apnea cannot be repleted, the subsequent portion of the fall in arterial oxygen saturation as measured by a pulse oximeter over time will be directly correlated to the oxygen consumption of the patient. The average oxygen consumption of a resting human (approx. 3.5 ml/kg/min) has a relatively constant relationship to average body arterial oxygen stores (approx. 25 ml/kg). Although substantial variability exists in body oxygen stores in chronically ill patients with low cardiac output states (resulting in lower mixed venous oxygen storage), a finite range of oxygen stores exists. Indeed, even in the presence of severe compensated disease, mixed venous oxygen saturation generally ranges from 50%–80%. Therefore, a sleeping human has a definable and predictable range of slopes of arterial oxygen saturation decrement as a function of the baseline mixed venous oxygen saturation initially and of oxygen consumption and body oxygen stores terminally. Although augmented body muscular activity associated with obstructive apnea could modestly increase oxygen consumption and although a decrease in oxygen consumption may occur below a critical levels of tissue oxygenation, the declining range of slope of desaturation is still predictable within only modest variances.

To understand the predictable parameters of arterial pulse oximetry waveform, it is important to consider the way in which pulse oximetry reflects total body oxygen stores. Total body oxygen stores can be conceived as representing four major compartments:
1. The Lung Compartment,
2. The Arterial Compartment,
3. The Tissue Compartment, and
4. The Venous Compartment.

Oxygen enters the lungs and is stored sequentially in each of these compartments. When oxygen is depleted during apnea, depletion occurs first in the tissue compartment, second in the venous compartment, third in the lung compartment, and fourth in the arterial compartment. Whereas, when oxygen is repleted, oxygen appears first in the lung compartment, second in the arterial compartment, third in the tissue compartment, and fourth in the venous compartment. It can be seen, therefore, that since pulse oximetry measurements reflect oxygen stored within the arterial compartment, if sequential depletion of arterial saturation occurred due to phasic apneas that the initial apneic episode would result in depletion of the arterial compartment only after the substantial depletion of other compartments has developed.

Using the above, the inventor of the present invention realized that he could predict with reasonable certainty whether or not a desaturation occurring during a continuous nocturnal oximetry measurement falls within the anticipated range of parameters which define the slope of arterial oxygen desaturation of hemoglobin which can physiologically occur during an apneic episode. In this manner, each desaturation episode can be defined, as a function of the characteristics of the waveform of deflection, as either consistent with an apneic episode or inconsistent with an apneic episode. Saturations which decrease too rapidly to be accounted for on the basis of physiologic oxygen depletion due to apnea would be identified as inconsistent with an apneic episode and therefore identified as being secondary to artifact. On the other hand, the desaturation episodes which decrease too slowly to be accounted for on the basis of physiologic oxygen depletion and would be identified as inconsistent with an apneic episode and therefore secondary to either hypoventilation, alterations in ventilation perfusion matching, or to artifact. The means for identifying a desaturation event is preferably a processor; and according to the first embodiment of this invention, as described above, the processor compares a calculated slope of the event with a value of slope which is determined in advance to be indicative of sleep apnea. A diagnosis of sleep apnea is made based on that comparison.

Figure 1:
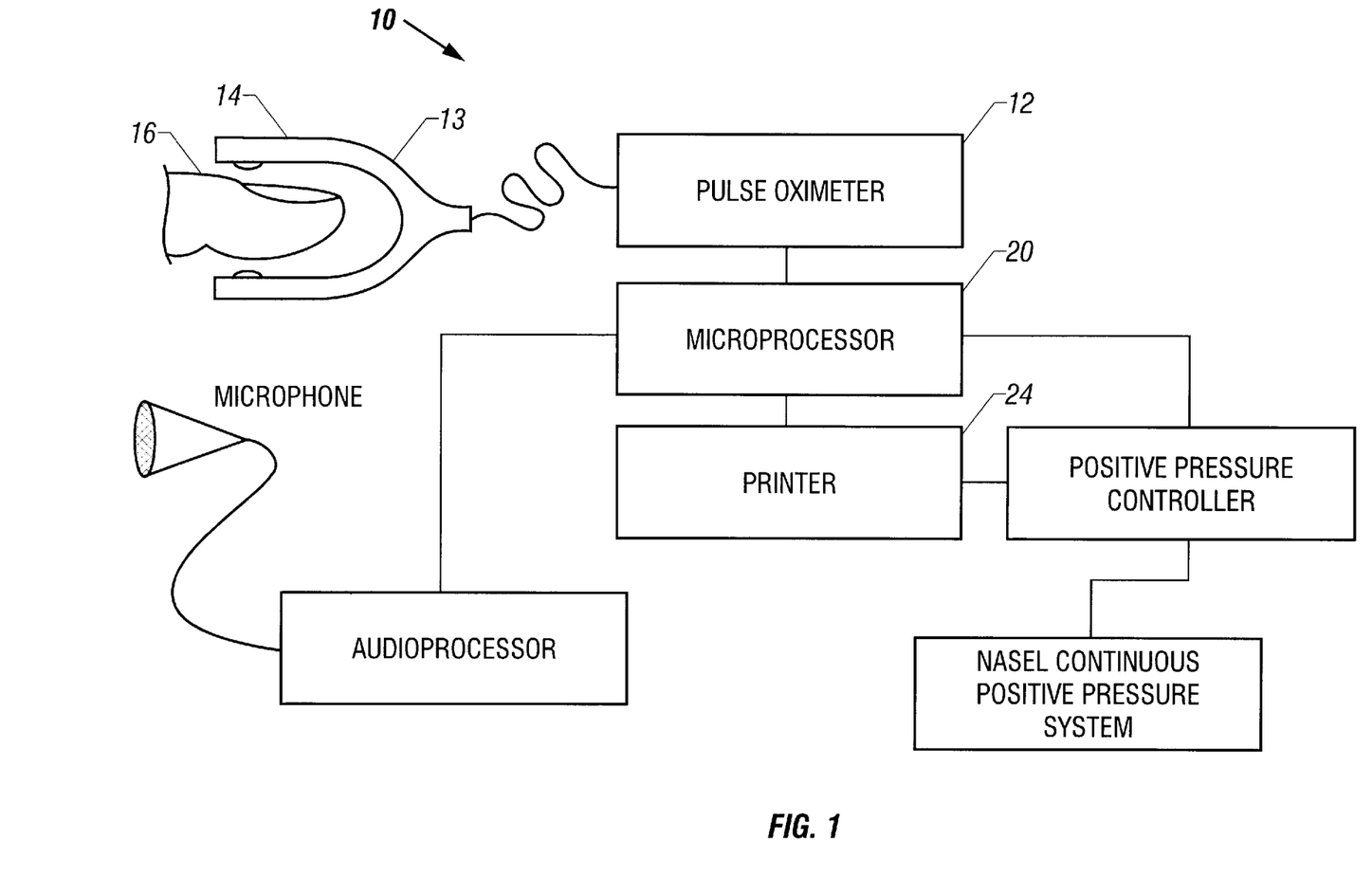
FIG. 1 shows a block diagram of the basic system of the present invention.

More specifically, the preferred embodiment of the sleep apnea diagnosis system 10 of the present invention is shown in FIG. 1. It includes a conventional pulse oximeter (12) with a probe (13) for transillumination or reflection from a human body part such as a finger (16). The oximeter is connected to a microprocessor (20) which records oxygen saturation and pulse as a function of time. A printer (24) is connected to the microprocessor. The microprocessor analyzes the oxygen saturation values as a function of time, as will be discussed in detail herein. In one preferred embodiment, the system is used in the following way:

The microprocessor is disposed in connection with the oximeter with a probe and printer for recording the oxygen saturation as a function of time, and the oximeter probe is attached to a patient. The oxygen saturation of hemoglobin is recorded as a function of time while the patient sleeps.

Figure 2:
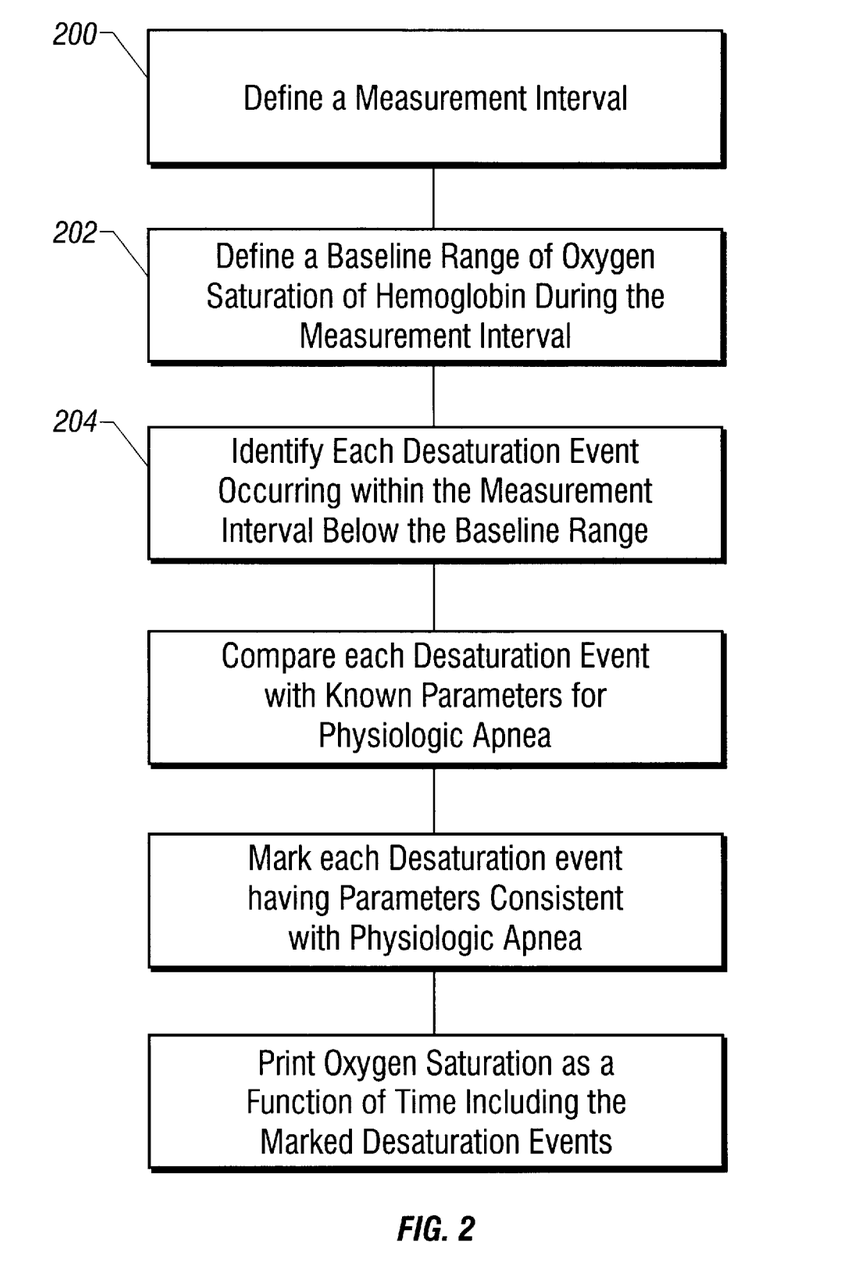
FIG. 2 shows a basic flowchart of operation of the present invention.

A measurement interval of, for example, 10 minutes is defined along the sleep recording as shown in step 200 of FIG. 2. Step 202 defines a mean maximum baseline range of oxygen saturation of hemoglobin (±3% saturation) is defined over the measurement interval.

A desaturation event can be defined as at least a 4% substantially uninterrupted decrement in saturation below the defined baseline mean of oxygen saturation. A lower percentage can be used to increase sensitivity. Each desaturation event is identified in step 204, and the desaturation change of each desaturation event is measured. The desaturation interval is defined as the duration of the uninterrupted decline in saturation of each desaturation event.

Then, slopes are calculated. The descending slope of each desaturation event is calculated as:

$\Delta S_D / \Delta T_D$ where:

$\Delta S_D$=Desaturation change (in % saturation;

$\Delta T_D$=Desaturation interval (in seconds).

A resaturation event is defined as a substantially uninterrupted rise in saturation which terminates the declining slope of the desaturation event. The resaturation change of each resaturation event is also measured.

The resaturation interval is measured as the duration of the uninterrupted rise in saturation of each resaturation event. The ascending slope of each resaturation event is calculated as:

$\Delta S_R / \Delta T_R$.

where:

$\Delta S_R$=Resaturation change (in % saturation);

$\Delta T_R$=Resaturation interval in seconds.

A phasic desaturation event is defined using all coupled desaturation and resaturation events wherein the sum of the duration of the desaturation event and the resaturation event is less than 3.5 minutes and wherein the descending slope falls within a finite range of between 1.3%/sec and 0.3%/sec.

The descending to ascending saturation slope ratio of each phasic desaturation event is calculated as:

$(\Delta S_D / \Delta T_D) / (\Delta S_R / \Delta T_R)$.

The number of probable apneic events within the measurement interval is defined as the number of phasic desaturation events falling within the finite range of ascending to descending slope ratios of between 3.5–10.5.

Each probable apneic event is marked with the identity marker, PA, and the above steps are repeated for each additional 10 min. interval along the recording for the entire sleep recording.

Then, appropriate action is taken: either the pulse oximetry waveform is printed as a function of time with each probable apneic event marked PA for identification, or treatment of sleep apnea is either manually or automatically administered.

The probability that a patient has sleep apnea will be a direct function of the number of phasic desaturations which meet the above criteria for sleep apnea per hour of recording and this probability can be calculated and printed.

Therefore, in the preferred embodiment, each desaturation event is identified as to whether or not it meets the criteria for physiologic apnea. The number of events per hour are then calculated and then printed. Each desaturation event which has been identified by the microprocessor as consistent with a physiologic apnea is so marked (such as PA for probable apnea or PCA for physiologically consistent with apnea). The pulse oximetry waveform in the preferred embodiment is then printed to provide a hard copy. This printed hard copy includes identification of each desaturation event which has been determined by the microprocessor as consistent with a physiologic apnea. In addition, the presence of desaturation slope acceleration, as will be discussed, by comparing closely spaced consecutive desaturation slopes as in FIG. 4 and such identification also provided on the printed hard copy.

This invention therefore provides a compact, single device which is easily suitable for home use and can be simply taken home by the patient and interfaced with a body part, such as a finger, to provide both screening and a mechanism to provide a specific diagnosis of sleep apnea with a single overnight recording. The hard printed copy provides graphical data which can be overread by the physician since the computer specifically identifies the desaturation events which have been interpreted as consistent with sleep apnea. This provides the physician with the opportunity to determine whether he or she agrees with the diagnostic interpretation of the microprocessor.

The diagnosis can be treated by repeating the sleep recording during nasal CPAP (Continuous Positive Airway Pressure) therapy. The identification of multiple desaturations with patterns as defined above which are consistent with the physiology of apnea and which are eliminated by nasal CPAP therapy is diagnostic of apnea and further establishes the parameters defining effective treatment requirements.

The invention includes the system taking additional action based on the identification of the diagnosis of sleep apnea based on the above slope comparison. The action can include, as in FIG. 1, the microprocessor activating a range of nasal continuous airway pressures through a pressure controller within defined limits to automatically and effectively treat a patient's sleep apnea once the diagnosis of sleep apnea has been made by the microprocessor. Activation of flow is initiated by the microprocessor on identification of multiple sleep apnea-related desaturations meeting the criteria as descried above. The pressure can be titrated upward by, for example 1–2 cm $H_2O$ pressure increments by the microprocessor upon identification of multiple consecutive desaturations which are not effectively eliminated by the starting pressure.

In this way, the invention greatly enhances the diagnostic sensitivity and specificity of nocturnal oximetry in the diagnosis of sleep apnea and to further utilize the identification of oximetry-derived desaturation events to trigger the storage and/or collection of additional sensory data concerning each desaturation event and; furthermore, the system can be utilized to automatically initiate and adjust therapy to mitigate further desaturation events.

In addition to a definable descending desaturation slope, oximetry measurements during apnea periods have other definable and predictable parameters. Importantly, apneic episodes have a definable and predictable range of duration. It is clear that brief apneic episodes, for example with brief breath holding does not result in significant arterial oxygen desaturation as measured by pulse oximetry. However, when apneic periods are prolonged as with obstructive sleep apnea, oxygen desaturation progressively declines as a function of factors, as previously discussed. Unless such an apneic episode is limited in duration, the patient would die from hypoxemia. Therefore, each desaturation which occurs as a function of apnea will have a phasic quality with a predictable range of duration. A second aspect of the invention analyzes the duration of the apneic episode to determine if it is of a duration likely to indicate sleep apnea.

The range of duration generally does not exceed three minutes. Therefore, for a desaturation event identified by pulse oximetry to be secondary to an apneic episode, it should preferably have a duration. of less than three minutes. Oxygen desaturations due to sleep apnea should be terminated with the resaturation of recovery within 3–3.5 minutes or less. Oxygen desaturation events which occur for greater than three minutes are identified as either secondary to hypoventilation, ventilation perfusion mismatching, or artifact.

Another aspect of the invention is based on the recognition that an apneic episode which occurs during sleep is generally reversed by an arousal. At this point, the patient's central nervous system increases upper airway tone and atmospheric gas rapidly enters the lungs and exchanges with the oxygen depleted gas within the alveoli. This exchange occurs within a few seconds. Since mixed venous blood in pulmonary capillaries rapidly equilibrates with the partial pressure of oxygen in the alveoli, arterial oxygenation will recover within seconds of the repletion of oxygen within alveoli. It should be noted that the amount of time required for blood to pass from the pulmonary capillaries to the peripheral site of pulse oximetry measurement can be measured is very brief. Therefore, the ascending slope of oxygen saturation during recovery from an apneic episode is extremely rapid. Ascending slopes which are not rapid are unlikely to be secondary to repletion of oxygen partial pressure within alveoli associated with arousal from an apneic episode and rather may be secondary to a crescendo of increasing respirations following a hypoventilation episode as in Cheyne-Stokes respirations or may be secondary to improvement in ventilation perfusion matching. In a recent study performed by the present inventor the mean slope of desaturation was 0.8% per second, with all desaturation slopes ranging between 0.3% per second and 1.1% per second. The mean slope of recovery 7.6% per second, with recovery slopes ranging from 2.5% per second to 8.3% per second. The mean recovery to apnea slope ratio was 7.66, with a range of 3.8 to 10.4. Hence, in yet another aspect of the invention, the resaturation slope, immediately following the desaturation, is also determined, and used in the diagnosis of sleep apnea.

Additional ways of comparing the calculated slope with a value of slope which is determined in advance to be indicative of sleep apnea include using other parameters to enhance the specificity of continuous nocturnal oximetry in the diagnosis of sleep apnea include comparisons of consecutive desaturation slope values and the identification of alterations in desaturation values as a function of events occurring immediately prior to the desaturation event.

Since obstructive sleep apnea events occur by similar physiologic process each time within the same patient, consecutive desaturation events will commonly have similar desaturation slopes. The identification of these consecutive desaturation events having similar desaturation slopes which have values consistent with physiologic apnea provides additional evidence supporting these events as secondary to cyclic obstructive sleep apnea.

Furthermore, the preceding desaturation event can effect the shape and the slope of the desaturation event which immediately follows. That is, preceding desaturation event may accelerate the initial portion of the slope of the following desaturation. Although other factors may contribute to the development of this increase in desaturation slope, the primary factor appears to be the depletion of body oxygen stores where insufficient time has developed for repletion for tissue and venous oxygen stores. In other words, during rapidly cycling apneic events, recovery time may be inadequate to replete all body oxygen stores. However, the pulse oximeter is measuring arteria oxygen saturation. Therefore, after repletion of oxygen stores within the lung, arterial oxygen saturation rapidly rises before venous oxygen stores have been repleted. If an apneic event recurs before the restoration of venous oxygen stores, this apneic event will be superimposed upon substantially depleted total body oxygen stores despite the fact that pulse oximetry may demonstrate normal arterial oxygen saturation. Since at this time apnea is occurring in the presence of markedly depleted body oxygen stores (i.e. a much lower mixed venous oxygen saturation), the initial portion of the slope of the declining arterial oxygen saturation may be substantially greater than the slope of the decline of oxygen saturation which occurred during the preceding desaturation event. This phenomenon would not be expected to occur in association with artifact and would only be expected to occur in the presence of rapidly cycling changes in body tissue oxygen stores. Consecutive closely spaced desaturation events, therefore, interact so that the first desaturation event can affect the waveform of the second desaturation event provided the interval between the two events is short enough and the level of desaturation occurring in the first event is substantial enough to result in a sizable depletion of total body oxygen stores.

The greatest portion of oxygen storage is within the venous compartment. At any given time, therefore, the amount of global oxygen stored is, in large part, a function of the extent of excess of oxygen delivered to the tissues which is stored within the venous pool. In the absence of arterial hypoxemia or profoundly compromised cardiovascular function, oxygen delivery substantially exceeds oxygen demand; resulting in considerable oxygen stores within the mixed venous pool. The amount of oxygen stored within the mixed venous pool can, therefore, be seen as a dynamically-stored, hidden buffer which mitigates the decline in saturation attendant any change in alveolar ventilation. Although patients with profoundly decreased mixed venous oxygen saturations would be expected to have a more rapid and greater fall in arterial oxygen saturation for any given level of change in alveolar ventilation, this still falls within a definable range.

During very rapidly cycling apneas (i.e. apneas occurring within less than 10–20 seconds of each other), body oxygen stores can be seen therefore as a moving wave through consecutive body compartments wherein the first wave affects the configuration of the second wave. The identification of this effect should be virtually diagnostic of rapidly cycling sleep apnea and this phenomenon can be exploited to assist in the specific diagnosis of sleep apnea utilizing the recording of nocturnal oximetry alone.

Desaturation slope acceleration may occur when cyclic apneic events occur within less than 10 seconds of each other and when the depth of arterial saturation associated with the first cyclic event is greater than 15%. The inter-desaturation event intervals can be defined specifically as that point wherein the first desaturation event recovers substantially to baseline to the point in time when the second desaturation event begins to decline from the baseline.

It can be seen, therefore, that a declining waveform of arterial oxygen desaturation in severe sleep apnea can be expected to have two major physiologically-derived components: 1) the slope of the initial declining limb which is primarily a function of the level of mixed venous oxygen saturation at the onset of apnea and the amount of exchangeable oxygen in the lung remaining after the onset of apnea. 2) the slope of the second component or terminal limb is primarily a function of global oxygen consumption relative to body oxygen stores. (The terminal limb may not be present if apnea is brief.) The slope of the initial and terminal limb are generally similar in patients with normal mixed venous oxygen saturations. However, in patients with significantly low mixed venous oxygen saturation, the initial limb may have a much greater slope than the terminal limb, producing an angled appearance suggesting antecedent depletion of mixed venous oxygen stores.

The magnitude of the oxygen deficit which is derived from the preceding apneic event less the intervening excess oxygen uptake which attenuates this deficit between the apneas defines the magnitude of the slope acceleration of the initial limb of the after-following desaturation event. Therefore, an interval of oxygen deficit is present following a sustained apnea but it is hidden since arterial oxygen saturation is normal.

Figure 3:
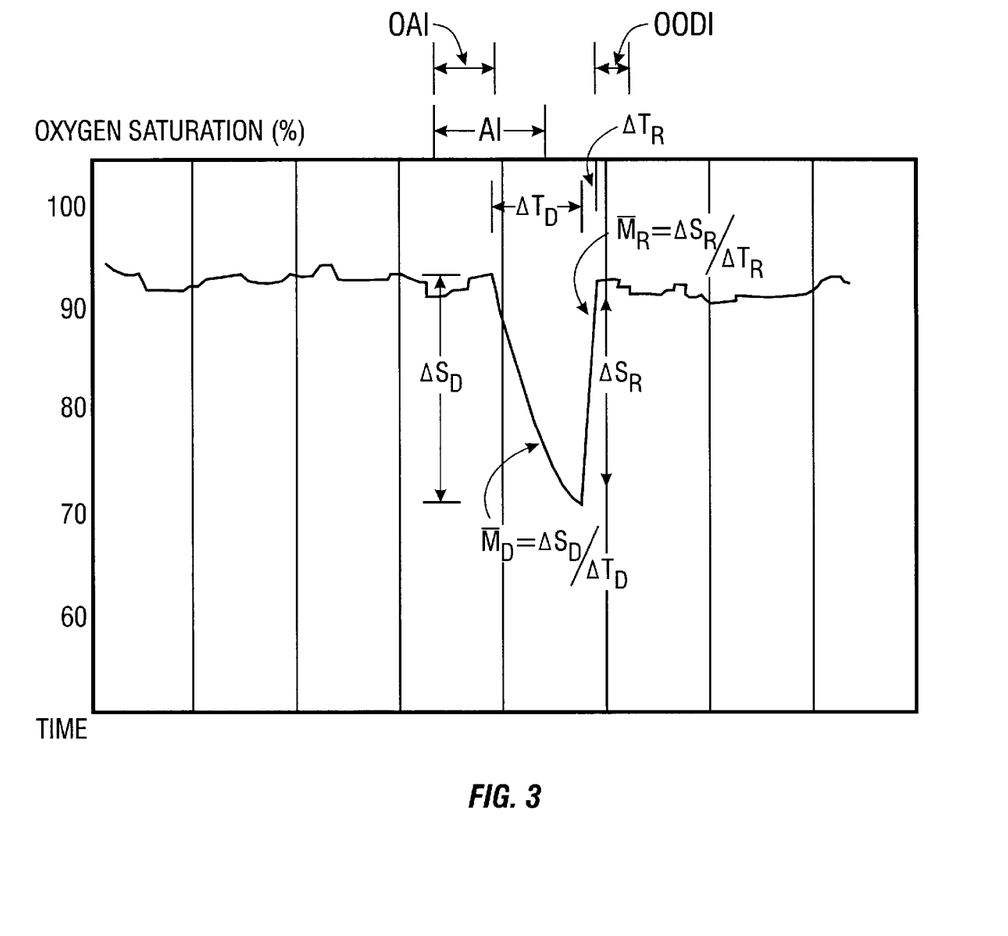
FIGS. 3 and 4 show basic desaturation events and many of the parameters associated therewith.
Figure 4:
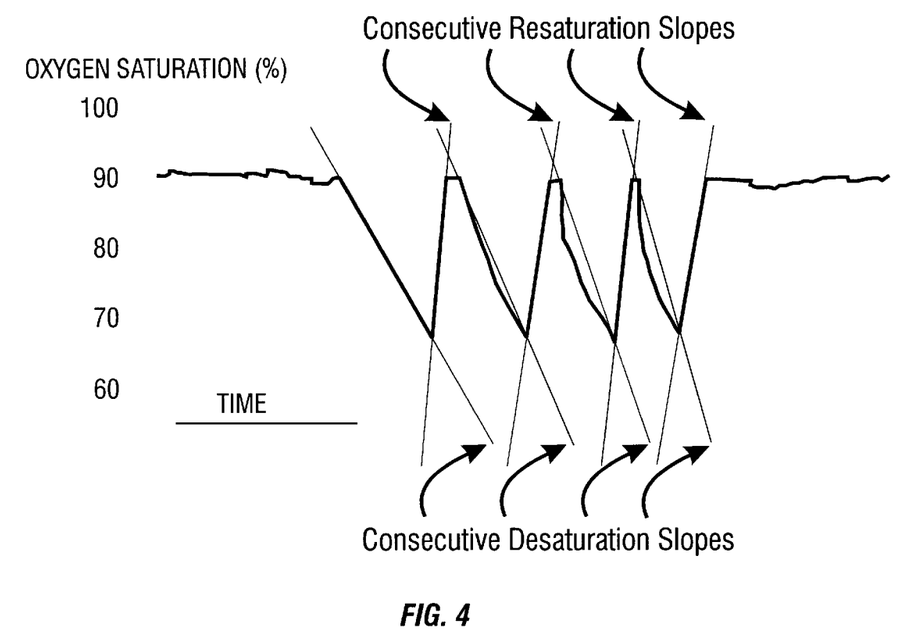

FIGS. 3 and 4 illustrate a desaturation event and many of the parameters as discussed supra which define the event. The parameters shown include:

$\Delta S_D$ Fall in saturation (in % sat.)

$\Delta S_R$ Rise in saturation (in % sat.)

$\Delta T_D$ Duration of the fall in Saturation/desaturation (in seconds)

$\Delta T_R$ Duration of the rise in saturation/resaturation (in seconds)

$M_D = \Delta S_D/\Delta T_D$ = Mean Slope of Desaturation $M_R = \Delta S_R/\Delta T_R$ = Mean Slope of Resaturation.

We also define the following terms:

AI The apnea interval—(the actual time wherein the patient experiences cessation of airflow which precipitates oxygen desaturation.)

OAI The occult apnea interval—(the interval wherein apnea has occurred; however, arterial oxygen stores are maintained by a shift of oxygen stores form the lung and venous compartment into the arterial compartment hiding the fall in body oxygen stores with respect to the oximetry measurement.)

OODI The occult oxygen deficit interval—(the interval immediately following return of oxygen saturation to near baseline after a desaturation event and wherein mixed venous oxygen desaturation persists. If a second apnea occurs within this interval, the slope of desaturation may be increased).

Using these parameters and realizations discussed supra, the inventor of the present invention made a system and technique which automatically analyzed the waveform pattern of continuous nocturnal oximetry, to specifically identify the presence or absence of moderate to severe obstructive sleep apnea-induced arterial oxygen desaturation. Such a system and technique makes it possible to diagnose moderate to severe obstructive sleep apnea with confidence with a single channel recording of nocturnal oximetry alone avoiding the need for complex and expensive polysomnography in the diagnosis of this disorder. The system and technique includes a mechanism to achieve the measurement of a compendium of parameters which are repetitively measured and analyzed, each improving the specificity of the diagnosis.

A summary of one such technique is as follows:

1. Dispose a microprocessor in connection with the oximeter with a probe and printer for recording the oxygen saturation of hemoglobin as a function of time.

2. Attach the oximeter probe to a patient.

3. Define a measurement interval.

4. Define the mean maximum baseline range of oxygen saturation of hemoglobin over the measurement interval.

5. Define a desaturation event as at a specific uninterrupted decrement in saturation below the defined baseline range of oxygen saturation.

6. Measure the duration of the uninterrupted decline in saturation of each desaturation event.

7. Calculate the descending slope of each desaturation event.

8. Define a resaturation event as an uninterrupted rise in saturation which terminates the is declining slope of the desaturation event.

9. Calculate the ascending slope of each resaturation event.

10. Define a phasic desaturation event as all coupled desaturation and resaturation events wherein the sum of the duration of the desaturation event and the resaturation event is less than a specified value and wherein the descending slope falls within a finite range.

11. Calculate the descending to ascending saturation slope ratio of each phasic desaturation event.

12. Define the number of probable apneic events within the measurement interval by comparing said calculated slope with a value of slope which is determined in advance to be indicative of sleep apnea, using any of the above techniques.

13. Identify each probable apneic event with an identity marker, or alternatively mark each event by its descending slope or by the slope ratio.

14. Treat the sleep apnea, either automatically, or manually, based on a diagnosis.

15. Repeat steps 1–14 to confirm the diagnosis and efficacy of treatment.

The above system represents the general concepts of one embodiment of the present invention. Other comparisons which incorporate the desaturation slope and the resaturation slope are also included within this teaching.

Figure 5:
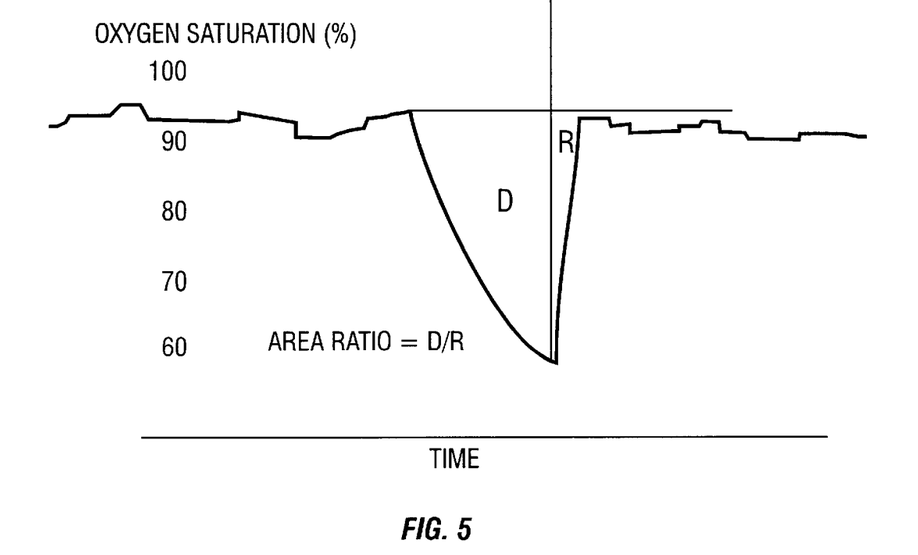
FIG. 5 shows a specific way in which a comparison can utilize the calculation of the area above each desaturation event compared to area above each coupled resaturation event.

For example FIG. 5 shows how a comparison can use the calculation of the area above each desaturation event compared to area above each coupled resaturation event. With this system, an x-axis is projected from a point of initial desaturation. A second y-axis is projected upward from the initial point of rise of saturation which signifies the onset of a resaturation event. The areas above the sloping lines, defined as D and R in the above figure, are then compared in a similar manner to that described in the previous embodiment.

In addition, the specificity and sensitivity of oximetry with respect to the diagnosis of sleep apnea is greatly enhanced by another embodiment of the invention which includes all of the multiple slope comparisons as described above. In such a system, in combination, the desaturation slope is compared to a desaturation slope which is consistent with a diagnosis of sleep apnea; second, the resaturation slope is compared with resaturation slopes known to be consistent with sleep apnea; third, desaturation slopes are compared with coupled resaturation slopes to define a slope index which is known to be consistent with sleep apnea; fourth, desaturation slopes and resaturation slopes are compared with other such slopes within the same record to identify slope similarity of the desaturation slopes and slope similarity of the resaturation slopes, respectively; furthermore, the similarity of the desaturation-resaturation slope index of the identified events can be compared; furthermore, as previously discussed, consecutive slopes can be compared in relationship to the interval between desaturation events to determine whether a preceding desaturation event affects the slope of a closely after following desaturation event, and; finally, the mean of all desaturation slopes can be compared to the mean of all resaturation slopes to define an aggregate index.

In another embodiment, the present invention identifies a phasic desaturation event to trigger storage or collection of at least one additional parameter of the patient. These additional parameters can be, for example, a recording of sound or video. When the microprocessor identifies specific coupled desaturation-resaturation parameters which are physiologically consistent with sleep apnea, the microprocessor initiates the storage of selected data collected by at least one additional sensor.

Sound has been shown to be an important indicator of airway obstruction, however, many patients spend the majority of their night without major obstructive apneas. Therefore, if the entire night of sound were recorded, it would include a large amount of unnecessary sound recording, for only a small amount of useful data surrounding obstructive apneas. In the preferred embodiment shown in FIG. 1, the additional sensor includes a microphone 30 which can be integral with or carried by the probe 13 of the pulse oximeter 12 or which can be positioned in other regions near the patient during sleep. With this preferred embodiment, the microphone 30 is connected to an audio processor 32 of any known type, such as a Sound Blaster(™) 16-bit processor. The sound is recorded digitally as a function of time. Alternately, the sound may be Fast Fourier transformed ("FFT"), and the transform information may be stored. Alternatively, other means of sound or other recording can be utilized.

Preferably, the sound is continuously recorded throughout the night and the most recent recording always maintained in short-term memory. If, after a finite period of time (for example, 4 minutes), no coupled desaturation-resaturation event occurs which is specific for sleep apnea, the oldest part of the recorded sound will be erased or otherwise not marked for retrieval. If, however, a coupled desaturation-resaturation event occurs which is consistent with sleep apnea, the identification of this event will trigger the marking and storage of the collected sound data during an interval preceding, during, and immediately after the event.

In the preferred embodiment, the total sound interval retained for each desaturation event includes the interval of the coupled desaturation-resaturation event, as well as one minute preceding and one minute following each such event; although this recording time can be further reduced for greater efficiency of memory utilization. In this way, the entire night will be monitored by oxygen saturation while sound is stored, but the information can be rejected to save memory unless a sleep apnea event is identified by pulse oximetry. If a sleep apnea event is identified, this will trigger the long-term storage of sound information surrounding that event. In this way, the efficiency sampling of sound that can be greatly enhanced since only small portions of sound need be collected in relationship to each apnea event.

Continuous recording of oxygen saturation and sound when indicated as a function of time can be digitally stored on any commercially availible removable computer memory media, for example, a high-capacity floppy disc, or a removable Bernoulli disc, and then transported to a second microprocessor for evaluation by the physician and for printing. The entire record can be printed with a continuous graphical representation of oxygen saturation as a function of time. The sound can be graphically represented as a function of time by (for example, showing the volume as the width of the line and the frequency as its position along the y-axis). As discussed previously, such graphical representation of oxygen saturation can include specific markers indicating coupled desaturation and resaturation events which are physiologically consistent with sleep apnea.

Preferably, staccato or interrupted low frequency sounds may also be graphically represented preceding an oxygen desaturation event. Subsequently, variable high frequency sounds of low volume may be identified immediately preceding the recovery of oxygen saturation, indicating the presence of post-apnea hyperventilation. The physician can easily, therefore, determine whether these oxygen desaturation events are due to obstructive sleep apnea by identifying the sound parameters with which these coupled desaturation-resaturation events are temporally associated. Of course, all coupled desatruation events might not necessarily be associated with a typical sound pattern. However, throughout the night recording, patients with obstructive sleep apnea would be expected to have typical snoring sounds; whereas, patients with central sleep apnea from a periodic breathing or alterations in ventilation-perfusion mismatch would not be expected to demonstrate such sound parameters in relationship to such coupled desaturation-resaturation events.

The system is further advantageous in that it allows the physician to efficiently focus on portions of the night which are of the greatest interest. For example, the physician can specify a desaturation event identified by the microprocessor as an apnea, then either look graphically at the sound surrounding that event or, alternatively, listen to digitally-recorded sound which surrounds a specific desaturation-resaturation event. It should also be clear that a video recorder could be activated in a similar manner, along with a sound recorder, to obtain critical bytes of a night's sleep for efficient evaluation. In this way, the diagnosis of airway obstruction can be confirmed, along with the diagnosis of sleep Apnea, by utilizing a greatly simplified and less expensive system than conventional home polysomnography.

It is clear that, because of overlap with other disorders, the diagnosis of mild sleep apnea cannot be achieved by identifying a single coupled desaturation-resaturation event even when the event and all the associated slopes are physiologically consistent with sleep apnea. For this reason, the identification of a desaturation slope and a resaturation slope and a comparison of these slopes, even wherein all meet the criteria for sleep apnea, can only be said to identify an event that is physiologically consistent with apnea from the perspective of oxygen desaturation and resaturation waveform. It is the comparison of multiple desaturation events which is specific for sleep apnea as in the present invention.

Although, as per the previous embodiment, the analysis of slope parameters when multiple events are identified and counted is specific with respect to moderate to severe apnea, it is critical to achieve specificity for the large patient population that has only mild sleep apnea. Unfortunately, many disorders can produce oximetry waveform deflections which are repetitive and/or cyclical and of equivalent magnitude to those of mild sleep apnea.

Enhanced sensitivity must be achieved for patents with mild oximetry deflections due to sleep apnea. In addition to providing enhanced sensitivity it is important for a system to make a rapid diagnosis of the presence of instant sleep apnea for CPAP titration. The microprocessor must make a definitive and reliable assessment of the presence or absence of sleep apnea within a short interval to allow a higher number of upward CPAP titrations throughout the night to assure that the minimum opening therapeutic pressure has been identified, as will be discussed.

One preferred embodiment utilizes the continuous calculation and comparison of saturation slopes to identify sleep apnea to thereby enhance sensitivity for mild apnea and achieve rapid diagnosis of instant sleep apnea. In this embodiment, as is conventional, oxygen saturation is measured as a function of time and each saturation data point is stored as a function of the sampling frequency. The present invention then utilizes each new data point with a preset number of preceding data points (for example, four data points wherein the sampling frequency is 20 Hz) to derive a continuous instantaneous slope. The instantaneous slope is recorded as a function of time and can be plotted with saturation as a function of time on the same graph. In this preferred embodiment, the instantaneous slope is calculated as the slope of the line of best fit (as by conventional formulas) drawn through the specified number of saturation points, such as 3–5 data points. As each data point is added, the new slope is recorded as a function of this new data point with the first data point of the group deleted. This derives a continuous moving waveform of the calculated slope of oxygen saturation/second, which is shown graphically in FIG. 6. In the preferred embodiment, multiple consecutive slopes in the same direction are considered aggregate slopes and are averaged to produce a mean negative or positive aggregate slope. The continuous calculation and analysis of this slope waveform provides an enhanced specificity in the diagnosis of sleep apnea with minimal compromise in sensitivity since it is not dependent on a specific threshold deflection for the identification of apnea.

Since sampling frequency will determine the configuration of any oximetry waveform, the greater the sampling frequency, the more reliable will be the slopes in the presence of very mild sleep apnea. For mild sleep apnea, a sample recording interval of 3 seconds (wherein the lowest recorded saturation with this interval is recorded) is adequate, although a continuous sampling for each pulse is optimal for this diagnostic system.

In sleep apnea, oxygen desaturations generally occur within clusters. For the purpose of the present invention, a cluster is said to be present when at least three consecutive negative slopes interrupted by positive slopes have occurred wherein the intervening interval between each consecutive negative slope is less than two minutes. The present inventor has discovered that the presence of a cluster of at least three negative slopes meeting these criteria and wherein the consecutive negative slopes are similar (for example, falling within a range of the initial slope ±60%) and wherein the negative-positive slope ratios are within 3.5–10.5 is clearly diagnostic of a sleep apnea cluster and can be said to comprise a sleep apnea slope cluster complex, referred to hereinafter as a "slope cluster complex. " Such a slope cluster complex 50 is graphically shown in FIG. 6.

In the presently preferred embodiment, the identification of slope cluster complexes is used to facilitate CPAP titration. With this system, the microprocessor can initiate nasal positive pressure at, for example, a pressure of 4 cm of $H_2O$ upon identification of a slope complex. As is known in the art, this pressure can be incremented from an initial 0 pressure up to 4 cm of $H_2O$ pressure over a period of two to five minutes or longer to minimize the potential for arousal with initiation of therapy. Throughout this time, the pulse oximetry waveform is monitored for any evidence of further slope cluster complexes. If an additional slope cluster complex occurs after the CPAP has reached 4 cm of pressure, the microprocessor again increases the CPAP level by an additional 1 cm during the final negative slope of this new complex. If an additional after-following slope cluster complex again occurs the microprocessor again increments, the nasal CPAP pressure by an additional 1 cm during the final negative slope of this complex. The microprocessor will continue to monitor for further complexes and similarly, increment the nasal CPAP by 1 cm upon each recurrence up to a present pressure limit of, for example, 15 cm. When no further such complexes occur subsequent to an increment in CPAP, this level is maintained for a sustained period, which should preferably be equal to or exceed 15 minutes. If any further slope cluster complexes occur within this interval, the microprocessor will increment CPAP by 1 cm of $H_2O$ pressure and this pressure will be maintained until no further complexes are identified for 15 minutes. Once the baseline oxygen saturation has been without further slope cluster complexes for 15 minutes, the CPAP is eliminated by the microprocessor. This can occur slowly over a period of, for example 2 minutes, to minimize the potential for arousal to be induced by sudden reduction of nasal CPAP. The patient is then monitored again for evidence of recurrent slope cluster complexes, as previously described. If a slope cluster complex is again identified, the CPAP is incremented in a similar fashion to that previously described; however, to allow more rapid titration, the starting level of CPAP is set at a minimum of 2 cm $H_2O$ below the final therapeutic level, which level was achieved during the preceding titration. For example, if the preceding titration achieved a therapeutic CPAP of 10, the starting titration level for the titration would not be less than 8. (However, the CPAP unit can be ramped slowly up to 8 over a period of 30 seconds, rather than suddenly initiating this pressure.) Again, incremental CPAP titration is utilized for each consecutive slope cluster complex, as for the initial titration, until no further slope cluster complexes occur for the specified time interval of 15 minutes. After the interval of 15 minutes without a slope cluster complex has concluded, the CPAP will again be withdrawn, as previously described. The patient will be monitored and, if another slope cluster complex occurs, a new titration will be initiated. In this way, as many as 12 or more separate complete CPAP titrations can occur throughout the night. Actually, however, less CPAP titrations generally will occur in a majority of patients since often there are no more than 4–5 separate clusters of desaturation events in any single night. To increase the number of titrations, CPAP may be withdrawn after a shorter specified interval of absent slope cluster complexes, such as five minutes or upward titration may be more rapid, for example with each consecutive negative slope within a slope cluster complex after an initial 3 negative slopes have occurred. In this way, three or four CPA titrations may occur within a single 30 minute desaturation cluster.

The comparison of consecutive slopes within a cluster allows increased specificity with less loss of sensitivity by accepting the diagnosis of sleep apnea without requiring a specific magnitude of desaturation from the baseline. This is particularly true when the slope cluster complexes are obliterated by initiation or incrementation of the CPAP levels. There is, of course, a time delay between the development of apnea and the onset of oxygen desaturation identified by the pulse oximeter. Due to this delay, it is not generally possible to arrest a specific negative slope by the initiation or upward titration of nasal CPAP during said negative slope unless the initiation occurs within a very short interval after the negative slope has started. Even when initiated early, substantial desaturation will continue, even if complete elimination of the obstruction immediately occurs upon initiation. The initiation of nasal CPA) during a slope cluster complex, therefore, may effectively treat and prevent the next negative slope, but unless the slope is quite prolonged the initiation or upward titration of CPAP may not interrupt the negative slope which is already in progress since, indeed, the physiological mechanisms causing the negative slope may have already have been completed. Anticipating this delay (which may be 20 seconds or more) the CPAP can be initiated or titrated upward immediately upon identification of the third negative slope or at the end of the second negative slope. Arrest of the third negative slope after the expected delay can provide diagnostic value.

The purpose of this repetitive cyclic titration is to identify a breakpoint range of CPAP which provides adequate pressure to break a cycle of desaturations by preventing further apnea episodes. The effect is diagnostic and further identifies the level of CPAP required for longterm therapy. The presence of even very small desaturations, which occur with slope cluster complexes and which are consistently eliminated by a finite range of nasal CPAP pressures, is clearly diagnostic of sleep apnea and specifies the level of CPAP that is required for effective therapy. The recording of continuous CPAP pressure (as is known in the art), may be simultaneously performed and, the recurrent titration of the breakpoint can be identified by plotting the slope waveform simultaneously with CPAP to verify that actual breakpoints are occurring as a function of CPAP titration, rather than by chance. It is clear that with any single episode of titration, spontaneous cessation of sleep apnea cycles may occur at any time during the titration, providing an initial "breakpoint" which may actually not be truly a function of adequate therapy. However, the consistent identification of a single breakpoint range (for example, 8–10 cm) at which point, for example, four separate slope cluster complexes were terminated and wherein no further slope cluster complexes occurred when this level was maintained would clearly identify adequate therapy and would identify the lowest adequate therapeutic pressure.

Ideally, the entire titration process occurs over two nights. The initial titration process involves recurrent initiation and withdrawal of nasal CPAP, as previously described, over cycles of 15–30 minutes throughout the night. The microprocessor identifies the breakpoint pressure which is adequate to break all slope cluster complexes throughout the entire night's study. This pressure level is designated "the therapeutic breakpoint CPAP" level and is recorded and stored for the second night's study without requiring a second home visit or modem control for adjustment of the CPAP. Upon initiation of the second night's study the microprocessor automatically ramps the CPAP unit up to the therapeutic breakpoint CPAP value over a specified interval of, for example 5–30 minutes. The patient is then maintained on this pressure level throughout the night to assure the pressure is adequate.

Figure 6:
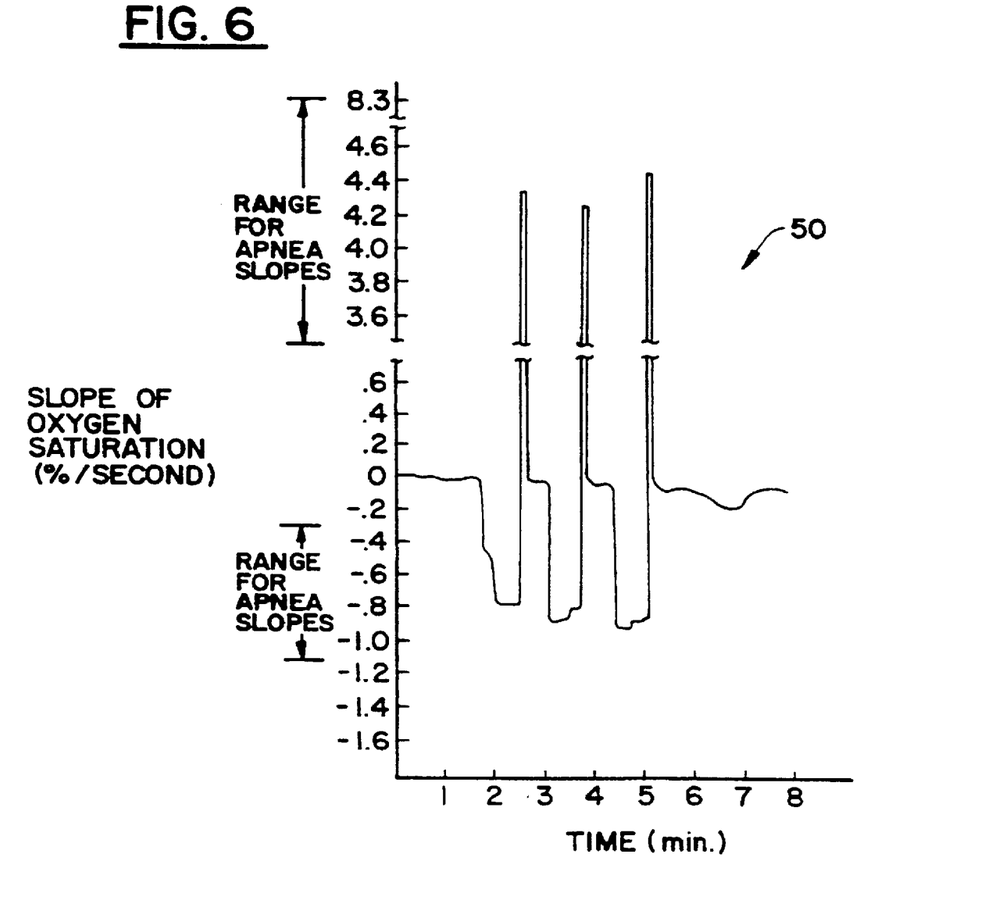
FIG. 6 shows a graph of oxygen saturation versus time which can be used to determine sleep apneas.

Importantly, for the sleep apnea diagnostic system to be utilized in clinical medicine, a hard copy must be produced so that the physician can overread the interpretation of the computer because many cardiac and pulmonary disorders, as well as artifact, can produce deflections with similar magnitude and configuration with that of mild sleep apnea. It is well known that differentiation of mild sleep apnea by visualizing the patterns of conventional oximetry waveform plots of oxygen saturation versus time is non-specific. The present invention describes a system which derives and analyzes continuously the multiple slope patterns to make a definitive diagnosis of sleep apnea quickly, however, for this to be accepted by the medical community, the physician must have a new way to interpret the oximetry tracing waveform and thereby overread the interpretation of the computer. The present inventor has discovered that the slope cluster complexes are easily visualized even in the presence of only mild apnea by graphically representing the continuous, instantaneous slope of oxygen saturation [as Δ Saturation (%)/Δ Time (seconds)] as a function of time, where slope is placed on the y-axis and time is placed on the x-axis. Utilizing this representation, the effect of the limited magnitude of the deflection is greatly minimized, and the effect of the particular slope characteristics are maximized graphically and visually. The effect of visually and graphically representing continuous slope as a function of time is shown in FIG. 6. This graphical representation allows the physician to overread the interpretation of the computer by identifying visually the presence of slope cluster complexes.

As noted, this graph demonstrates the slope of the oxygen saturation as a function of time where:

slope=change in saturation ΔS(%)/ΔT (seconds), and where time is in minutes.

The y-axis includes marked regions which identify slopes that are physiologically consistent with sleep apnea. For example, with respect to negative slopes, the physiologically consistent region is marked as −0.3 to −1.1 and with respect to positive slopes, the physiologically consistent region is marked as 2.5 to 8.3. As oxygen saturation data points are measured and stored, continuous slope calculations are made. Alternatively, consecutive negative or positive slopes may be defined as a single aggregate positive or negative slope and may be average for the purposes of graphical representation and interpretation.

The previously-described apparatus is both a diagnostic tool for sleep apnea and a fixed therapeutic pressure identifier. Specifically, it identifies the minimum fixed therapeutic pressure than can reliably prevent substantially all future apnea episodes in a given patient. This pressure is printed and identified as the minimum therapeutic break pressure or optimal nasal CPAP pressure. In the preferred embodiment, the microprocessor may set the nasal CPAP pressure on the nasal CPAP unit for long term therapy so that this pressure is subsequently maintained for this patient without further adjustment by patient, physician, or home health personnel. This therapeutic pressure which had been previously identified is, therefore, fixed and will be utilized, for example over the next 6–12 months, until a repeat study is performed at this pressure to confirm that further apneas have not redeveloped or that a lower pressure might be therapeutic (such as after weight loss).

While this language herein refers to oxygen saturation, it should be understood that gas exchange parameters could be determined in ways other than those specifically disclosed herein, but are included within the scope of this teaching. For example, sequential and cyclic time-dependent storage of carbon dioxide in body compartments during sleep apnea can be similarly used to diagnose sleep apnea using, for example, the comparison of consecutive slopes of maximum exhaled $pCO_2$. Also, inspiration-triggered variable pressures, such as BIPAP, may also be titrated in a similar manner to that described herein for CPAP.

Many modifications will become evident to those skilled in the art from this teaching and these modifications are included within the scope of this teaching.

What is claimed is:

1. A method for diagnosing sleep apnea comprising:

disposing an oximeter adjacent to a single human body part and recording a continuous measurement of oxygen saturation as a function of time to derive an oxygen saturation waveform;

identifying a first event comprising a desaturation event in which said oxygen saturation falls away from a baseline level by a predetermined amount and for a predetermined time;

identifying a second event comprising a resaturation event in which said oxygen saturation rises immediately following said desaturation, the presence of a consecutive desaturation event and resaturation event defining a couplet event;

identifying a third event comprising a second desaturation event occurring within a predetermined time interval after said resaturation and in which said oxygen saturation falls away from near said baseline level by near said predetermined amount, the presence of said first, second and third consecutive events defining a triplet event;

determining the number of said couplet events occurring during at least a portion of said measurement; and assessing the probability that a patient has sleep apnea based on said number of couplet events.

2. The method of claim 1 wherein said interval is defined as less than 2 minutes.

3. A method as in claim 1 further comprising the step of determining the number of said triplet events occurring during at least a second portion of said measurement and assessing the probability that a patient has sleep apnea based on said number of triplet events.

4. A method for diagnosing sleep apnea comprising:

determining an oxygen saturation of a patient's blood;

identifying a first desaturation event in which said oxygen saturation falls away from a baseline level by at least a predetermined amount;

calculating a slope of said desaturation event represented as the rate of change per unit of time of the fall of oxygen saturation;

comparing said calculated slope with at least one other value of slope of another desaturation event determined at a different time than said first desaturation event;

defining an interval of time after said first desaturation event;

when said other desaturation event occurs within said interval, determining whether the slope of at least an initial portion of said other desaturation event is greater than the initial portion of said first desaturation event, whereby the effect of said preceding desaturation event on the slope of the other desaturation event is determined; and diagnosing sleep apnea based on said comparing.

5. A method for identification of sleep apnea comprising the steps of:

disposing an oximeter adjacent to a single human body part and recording continuous measurement of oxygen saturation as a function of time to derive an oxygen saturation waveform as a function of time;

repetitively calculating slopes along said oxygen saturation waveform;

continuously comparing said slopes to a first predetermined range of slopes, and identifying a first slope comprising a desaturation slope which falls within said first predetermined range of slopes;

further comparing said slopes immediately following said desaturation slope to a second predetermined range of slopes and identifying a second slope comprising a resaturation slope which falls within the second predetermined range of slopes;

determining an area below a curve defined by the desaturation slope;

determining an area below the curve defined by the resaturation slope;

comparing said desaturation slope area with said resaturation slope area and using said comparison to determine said diagnosis of sleep apnea.

6. A sleep apnea treatment device, comprising:

an oximeter, having an output signal indicating an oxygen saturation of a patient's blood;

a processor element, responsive to said signal indicating oxygen saturation, for identifying at least two consecutive desaturation events in which said oxygen saturation falls away from a base line level by a predetermined amount and for a predetermined time;

said processor element identifying each desaturation event when it also includes a resaturation immediately following said desaturation event to thereby define a couplet event;

said processor element calculating a slope of each said desaturation event of said couplet event representing a rate of change per unit of time of fall of oxygen saturation;

said processor element calculating a slope of each said resaturation event of said couplet event representing a rate of change per unit of time of rise of oxygen saturation; and said processor element comparing said desaturation slopes with each other and for comparing said resaturation slopes with each other to identify slope similarity, and using said slope similarity to diagnose sleep apnea.

7. A sleep apnea diagnostic device, comprising:

an oximeter, having an output signal indicating an oxygen saturation of a patient's blood;

a processor element, responsive to said signal indicating oxygen saturation, identifying at least two consecutive desaturation events, in which said oxygen saturation falls away from a baseline level by a predetermined amount and for a predetermined time;

said processor element identifying each desaturation event which also includes a resaturation that occurs immediately following said desaturation event to thereby define a couplet event;

said processor element calculating a slope of each said identified desaturation event representing a rate of change per unit of time of fall of oxygen saturation;

said processor element calculating a slope of each said identified resaturation event representing a rate of change per unit of time of rise of oxygen saturation;

said processor element calculating a mathematical index of at least three said identified desaturation and resaturation slopes; and using at least the mathematical index to diagnose sleep apnea.

8. A method for evaluating a patient for diagnosis of sleep apnea using an oximeter having a sensor, the method comprising the steps of:

1) disposing said oximeter sensor adjacent a human body part, said oximeter having an output signal indicating an oxygen saturation of a patient's blood;

2) generating an oxygen saturation waveform as a function of time;

3) using a computer for:

a) repetitively calculating positive and negative oxygen saturation slopes along said oxygen saturation waveform;

b) determining whether at least three consecutive negative slopes interrupted by positive slopes occur where a time interval between each positive slope and the next negative slope following said each positive slope is less than a predetermined time interval, said occurrence defining a slope cluster complex, c) determining whether the value of said at least three negative slopes fall within a predetermined range, and d) using both said determinations to determine said diagnosis of sleep apnea.

9. The method of claim 8 wherein said predetermined time interval is two minutes.

10. The method of claim 8 further including using a computer for;
   a) comparing said negative slopes to said positive slopes,
   b) determining whether at least a portion of said negative slopes define lower rates of change of oxygen saturation than are defined by said positive slopes, and
   c) using said determination to determine said diagnosis of sleep apnea.

11. The method of claim 8 further including using a computer for the steps of:
   a) calculating a mathematical index of said negative slopes in relation to said positive slopes;
   b) determining whether at least a portion of said mathematical indices are within a predetermined range for said mathematical index; and
   c) using said determination to determine said diagnosis of sleep apnea.

12. The method of claim 11 wherein said mathematical index is a ratio having a range of about 3.5 to 10.5.

13. The method of claim 8 further including the steps of:
   a) upon both said determinations in steps b) and c), initiating a preset positive pressure to the nasal pharynx of said patient with a positive pressure device.

14. The method of claim 13 further including using a computer for the steps of:
   after the initiation of the positive pressure to the pharynx, determining whether a cluster complex reoccurs; and
   if said slope cluster complex reoccurs, repeating step d) at an increased level of said nasal positive pressure.

15. The method of claim 14 further including using a computer for the steps of:
   determining whether no slope cluster complex has occurred for a predetermined period and, if so, withdraw at least a portion of said positive pressure.

16. A method for determining an effective preset fixed pressure setting of one of a fixed single level and a fixed dual level positive pressure generating device for the long term maintenance treatment of sleep apnea, the method using an oximeter having a sensor, the method comprising the steps of:
   1) disposing said oximeter sensor adjacent a human body part, said oximeter having an output signal indicating an oxygen saturation of a patient's blood and a processor element responsive to said signal indicating oxygen saturation and generating an oxygen saturation waveform as a function of time;
   2) using a computer for repetitively calculating positive and negative slopes along said oxygen saturation waveform;
   3) determining whether two consecutive negative slopes interrupted by positive slopes occur where the time interval between each positive slope is less than a predetermined interval; and
   4) determining whether the value of said two negative slopes are within a predetermined range of each other so as to be characteristic of a slope cluster complex and using both said determinations to diagnose sleep apnea;
   5) upon both said determinations in steps 3) and 4) initiating a preset amount of positive pressure to the nasal pharynx,
   6) repetitively performing steps 3) and 4) to determine an effective positive pressure level which eliminates substantially all slope cluster complexes, and
   7) using said computer to indicate an effective fixed preset positive setting for long term use of a pressure generating device in the treatment of sleep apnea.

17. A method as in claim 16 further including the step of using said computer to automatically preset said determined fixed pressure on said pressure generating device for long term use.

18. A method for diagnosing sleep apnea said apnea producing at least one grouping of at least one oxygen saturation parameter, the method comprising:
   1) disposing said oximeter sensor adjacent a human body part, said oximeter having an output signal indicating an oxygen saturation of a patient's blood and a processor element responsive to said signal indicating oxygen saturation and generating an oxygen saturation waveform as a function of time; and
   2) using a computer for:
      a) determining the presence or absence of at least one grouping of repeating parameters along said oxygen saturation waveform,
      b) evaluating said at least one grouping and comparing said evaluation result to a range of evaluation results known to be consistent with sleep apnea,
      c) determining the intervening interval between consecutive repeating parameters within said grouping,
      d) comparing said intervening interval to a limiting range of intervening intervals known to be consistent with a sleep apnea related grouping, and
      f) determining the diagnosis of sleep apnea based on at least said evaluation result and said comparing said intervening interval.

19. A method as in claim 18 wherein said repeating parameter is the slope of the measured oxygen saturation as a function of time.

20. A method as in claim 18 wherein said repeating parameter is a negative deflection of the waveform and wherein the intervening time interval comprises the interval between said negative deflection and the next negative deflection.

21. A method as in claim 18 wherein two different parameters are compared.

22. A method as in claim 21 wherein one of said parameters is a positive deflection of the waveform and wherein another of said parameters is a negative deflection of the waveform occurring after said positive deflection, the intervening interval comprising the interval between said positive deflection and said negative deflection.

23. A method for diagnosing sleep apnea, said apnea producing at least one grouping of at least one oxygen saturation parameter, the method comprising:
   1) disposing said oximeter sensor adjacent a human body part, said oximeter having an output signal indicating an oxygen saturation of a patient's blood and a processor element responsive to said signal indicating oxygen saturation and generating an oxygen saturation waveform as a function of time; and
   2) using a computer for:
      a) determining the presence or absence of at least one grouping of a repeating parameter along said oxygen saturation waveform,
      b) evaluating said repeating parameter and comparing said evaluation result to a range of evaluation results known to be consistent with sleep apnea,
      c) determining the intervening time interval between consecutive repeating parameters within said grouping,
      d) comparing said intervening time interval to a limiting range of intervening time intervals known to be consistent with an sleep apnea related grouping,
      e) determining the frequency of said repeating parameters wherein both said evaluation result and said intervening time intervals are consistent with said parameters being caused by sleep apnea, and f) determining the diagnosis of sleep apnea based on at least said frequency determination.

24. A method for diagnosing sleep apnea, said apnea producing at least one grouping of at least one oscillating oxygen saturation parameter, the method comprising:

1) disposing said oximeter sensor adjacent a human body part, said oximeter having an output signal indicating an oxygen saturation of a patient's blood and a processor element responsive to said signal indicating oxygen saturation and generating an oxygen saturation waveform as a function of time; and 2) using a computer for:
   a) determining the presence or absence of said at least one grouping of said oscillating parameter along said oxygen saturation waveform,
   b) evaluating said grouping and comparing an evaluation result to a range of evaluation results known to be consistent with sleep apnea,
   c) determining the intervening interval between consecutive oscillating parameters within said grouping,
   d) comparing said intervening interval to a predetermined range of intervening intervals known to be consistent with a sleep apnea related grouping,
   e) determine the frequency of said oscillating parameters wherein both said evaluation result and said intervening intervals are consistent with said oscillating parameters being caused by sleep apnea, and
   f) determining the diagnosis of sleep apnea based on at least said frequency determination.

25. A method as in claim 24 wherein said oscillating parameter comprises a negative oxygen saturation followed by a positive deflection of the oxygen saturation.

26. A device for diagnosing the sleep apnea disorder in a patient, comprising:

a sensing unit capable of measuring a respiratory parameter during sleep, said respiratory parameter being of the type which has consecutive cycles of variation in said parameter indicative of a sleep apnea disorder and wherein each said consecutive cycle is induced by a corresponding consecutive apnea; and, a processor operating to:
   (a) record said parameter to derive a timed waveform indicative of said parameter,
   (b) identify at least one portion of said waveform in which said cycles are closely spaced to each other and define a cluster of said cycles, said cluster corresponding to a plurality of closely spaced apneas, and
   (c) diagnose sleep apnea based at least on said identifying of said cluster.

27. The device of claim 26 wherein said parameter is oxygen saturation of arterial blood.

28. The device of claim 27 wherein said cycle comprises a fall in oxygen saturation coupled to a rise in oxygen saturation.

29. The device of claim 28 wherein said fall in saturation defines a desaturation slope and wherein said desaturation slope falls within a specific slope range.

30. The device of claim 29 wherein said cluster includes at least three of said desaturation slopes.

31. The device of claim 30 wherein said cluster includes at least three of said resaturation slopes.

32. The device of claim 28 wherein said rise in saturation defines a resaturation slope and wherein said resaturation slope falls within a specific slope range.

33. The device of claim 26 wherein said cluster includes at least three of said cycles.

34. The device of claim 26 wherein, within said cluster, each consecutive cycle occurs within a maximum interval of the preceding cycle.

35. The device of claim 34 wherein said maximum interval is two minutes.

36. The device of claim 26 wherein said parameter is at least one property of exhaled gas.

37. The device of claim 36 wherein said parameter is maximum partial pressure of the carbon dioxide component of said exhaled gas.

38. A device for diagnosing a sleep apnea disorder in a patient, comprising:

a sensing unit and a processor, said device being capable of measuring a respiratory parameter during sleep and capable of recording said parameter as a function of time to derive a timed waveform of said parameter, said parameter being of the type wherein said sleep apnea disorder causes consecutive events of variation along said waveform, said events having a similar configuration, and wherein each of said consecutive events is induced by a corresponding consecutive apnea, said processor operating to:
   (a) identify at least one portion of said waveform in which said events are closely spaced to each other to define a cluster of said events, said cluster corresponding to a cluster of closely spaced apneas, and
   (b) diagnose sleep apnea based at least on said identifying of said cluster.

39. The device of claim 38 wherein said parameter is the oxygen saturation of arterial blood.

40. The device of claim 39 wherein said event comprises a fall in said oxygen saturation.

41. The device of claim 40 wherein said fall in saturation defines a desaturation slope and wherein said desaturation slope falls within a specific slope range.

42. The device of claim 41 wherein said cluster includes at least three of said desaturation slopes.

43. The device of claim 39 wherein said event comprises a rise in said oxygen saturation.

44. The device of claim 43 wherein said rise in saturation defines a resaturation slope and wherein said resaturation slope falls within a specific slope range.

45. The device of claim 44 wherein said cluster includes at least three of said resaturation slopes.

46. The device of claim 39 wherein said event comprises a fall in oxygen saturation coupled to a rise in oxygen saturation.

47. The device of claim 38 wherein, within said cluster, each consecutive event occurs within a maximum interval of the preceding event.

48. The device of claim 47 wherein said maximum interval is two minutes.

49. The device of claim 38 wherein said parameter is at least one property of exhaled gas.

50. The device of claim 49 wherein said parameter is the maximum partial pressure of carbon dioxide component of said exhaled gas.

51. A device for diagnosing a sleep apnea disorder in a patient, the device comprising an oximeter and a processor, said device being capable of measuring arterial oxygen saturation during sleep and of recording said saturation as a function of time to derive a timed waveform of oxygen saturation, said processor operating to:
   (a) repetitively calculate slopes along said oxygen saturation waveform;

(b) repetitively compare said slopes to a first predetermined range of slopes, and to identify a first slope comprising a desaturation slope which falls within said first predetermined range of slopes;

(c) further compare said slopes immediately following said desaturation slope to a second predetermined range of slopes and to identify a second slope comprising a resaturation slope which falls within the second predetermined range of slopes, said desaturation and said resaturation comprising a coupled event;

(d) repetitively perform operations a through c to repetitively identify additional coupled events said waveform;

(e) identify along at least one portion of said waveform wherein said events are closely spaced to each other to define a cluster of said events;

(f) diagnose sleep apnea based on at least said identifying of said cluster.

* * * * *